(12) United States Patent
Ruijters (10) Patent No.: US 11,864,869 B2
(45) Date of Patent: *Jan. 9, 2024

(54) APPARATUS FOR CHARACTERIZING A VESSEL WALL

(71) Applicant: KONINKLIJKE PHILIPS N.V., Eindhoven (NL)

(72) Inventor: Daniel Simon Anna Ruijters, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 3 days.

This patent is subject to a terminal disclaimer.

(21) Appl. No.: 17/548,505

(22) Filed: Dec. 11, 2021

(65) Prior Publication Data
US 2022/0095935 A1 Mar. 31, 2022

Related U.S. Application Data

(63) Continuation of application No. 15/767,778, filed as application No. PCT/EP2016/074118 on Oct. 10, 2016, now Pat. No. 11,202,575.

(30) Foreign Application Priority Data

Oct. 14, 2015 (EP) .................................... 15189794

(51) Int. Cl.
*A61B 5/02* (2006.01)
*A61B 5/00* (2006.01)
(Continued)

(52) U.S. Cl.
CPC .......... *A61B 5/02007* (2013.01); *A61B 5/026* (2013.01); *A61B 5/02014* (2013.01);
(Continued)

(58) Field of Classification Search
CPC ............ A61B 5/02007; A61B 5/02014; A61B 5/0215; A61B 5/026; A61B 5/055;
(Continued)

(56) References Cited

U.S. PATENT DOCUMENTS 6,309,359 B1 10/2001 Whitt
6,471,656 B1 10/2002 Shalman
(Continued)

FOREIGN PATENT DOCUMENTS

WO 199934724 A2 7/1999
WO WO-9934724 A2 * 7/1999 ......... A61B 5/02014
(Continued)

OTHER PUBLICATIONS

Levitt, M. et al "Cerbral Aneurysms Treated with Flow-Diverting Stents: Computational Models with Intravascular Blood Flow Measurements" American Journal of Neuroradiology, vol. 35, pp. 143-148, 2014.
(Continued)

*Primary Examiner* — Sean D Mattson (57) ABSTRACT

The invention presents an apparatus (6) for characterization of a condition of a vessel (12) wall of a living being (2). The relationship between temporal blood pressure (621) and blood flow (622) measurements of pulsatile blood motion within the vessel (12) is an indication of the health of the vessel (12) wall. Furthermore, the invention discloses a system (1) comprising the apparatus (6), and a method (100) of characterizing the condition of vessel (12) walls.

19 Claims, 8 Drawing Sheets

(51) Int. Cl.

| | |
|---|---|
| A61B 6/00 | (2006.01) |
| A61B 8/06 | (2006.01) |
| A61B 5/0215 | (2006.01) |
| A61B 5/026 | (2006.01) |
| A61B 5/055 | (2006.01) |
| A61B 8/08 | (2006.01) |
| A61B 8/00 | (2006.01) |
| A61B 6/03 | (2006.01) |
| A61B 8/04 | (2006.01) |
| A61B 8/12 | (2006.01) |
| G01R 33/563 | (2006.01) |

(52) U.S. Cl.
CPC ............ *A61B 5/0215* (2013.01); *A61B 5/055* (2013.01); *A61B 5/743* (2013.01); *A61B 6/03* (2013.01); *A61B 6/032* (2013.01); *A61B 6/4417* (2013.01); *A61B 6/504* (2013.01); *A61B 8/04* (2013.01); *A61B 8/06* (2013.01); *A61B 8/0891* (2013.01); *A61B 8/12* (2013.01); *A61B 8/4416* (2013.01); *A61B 2562/0247* (2013.01); *G01R 33/5635* (2013.01)

(58) Field of Classification Search
CPC ........... A61B 5/743; A61B 6/03; A61B 6/032; A61B 6/4417; A61B 6/504; A61B 8/04; A61B 8/06; A61B 8/0891; A61B 8/12; A61B 8/4416; A61B 2562/0247; G01R 33/5635

See application file for complete search history.

(56) References Cited

U.S. PATENT DOCUMENTS

| | | | |
|---|---|---|---|
| 11,202,575 B2 * | 12/2021 | Ruijters | ................. A61B 6/504 |
| 2002/0111554 A1 | 8/2002 | Drzewiecki | |
| 2003/0135124 A1 | 7/2003 | Russell | |
| 2005/0197571 A1 | 9/2005 | Mcveigh | |
| 2006/0241465 A1 * | 10/2006 | Huennekens | ........ A61B 6/5247 |
| | | | 600/458 |
| 2008/0319309 A1 | 12/2008 | Bredno | |
| 2011/0306867 A1 | 12/2011 | Gopinathan | |
| 2014/0003687 A1 | 1/2014 | Jou | |
| 2014/0005512 A1 | 1/2014 | Manwaring | |
| 2014/0066765 A1 * | 3/2014 | Fan | ..................... A61B 8/0891 |
| | | | 600/407 |
| 2014/0249386 A1 | 9/2014 | Caron | |
| 2015/0196250 A1 | 7/2015 | Nair | |

FOREIGN PATENT DOCUMENTS

| | | |
|---|---|---|
| WO | 2008139347 A1 | 11/2008 |
| WO | 2011158165 A2 | 12/2011 |
| WO | 2015085220 A1 | 6/2015 |

OTHER PUBLICATIONS

Bonnefous et al Quantification of Arterial Flow using Digital Subtraction Angiography, Medical Physics, vol. 39, No. 10, pp. 6264-6275, 2012.
Naeije, R. et al "Pulmonary Vascular Impedance in Microembolic Pulmonary Hypertension: Effects of Synchronous High-Frequency Jet Ventilation", Respiration Physiology, vol. 79, No. 3, Mar. 1990.
Ganesan, P. et al "Modelling of Pulsatile Blood Flow in Arterial Trees of Retinal Vasculature", Medical Engineering $ Physics, vol. 33, No. 7, 2010, pp. 810-823.
Pereira, V. Mendes et al "A DSA-Based Method using Contrast Motion Estimation for the Assessment of the Intra-aneurysmal Flow Changes Induced by Flow Diverter Stents", American Journal of Neuroradiology, vol. 34, 2014.
https://en.wikipedia.org/wiki/Fractional_flow_reserve, Feb. 2015.
Willemet, Marie et al Arterial Pressure and Flow Wave Analysis using Time-Domain 1-D Hemodynamics, Annals of Biomedicla Engineering, vol. 43, No. 1, Jan. 2015, pp. 190-206.
Illing, Lucas "Fourier Analysis", 2008.
Diehl, Rolf R. et al "Phase Relationship between Cerebral Blood Flow Velocity and Blood Pressure: A Clinical Test of Autoregulation", Stroke, vol. 26, No. 10, pp. 1801-1804, 1995.

* cited by examiner

APPARATUS FOR CHARACTERIZING A VESSEL WALL

CROSS-REFERENCE TO PRIOR APPLICATIONS

This application is a Continuation of application Ser. No. 15/767,778, filed Apr. 12, 2018, which is the U.S. National Phase application under 35 U.S.C. § 371 of International Application No. PCT/EP2016/074118, filed on Oct. 10, 2016, which claims the benefit of European Patent Application No. 15189794.9, filed on Oct. 14, 2015. These applications are hereby incorporated by reference herein.

FIELD OF THE INVENTION

The invention relates to an apparatus, a system and a method for measuring physical properties inside a body lumen.

BACKGROUND OF THE INVENTION

Weakening of an arterial wall may lead to formation of a bulge on the vessel wall. A large fraction of the population has asymptomatic aneurysms with no further growth of the bulge, presenting low risk for their condition. However, when the aneurysm evolves in size, the arterial wall weakens beyond a critical threshold due to the pressure exerted by the increasing volume of blood, resulting in rupture of the arterial wall and subsequent internal hemorrhage. After formation of an aneurysm, assessment of several physical properties as predictors of the aneurysm growth as well as the dynamic assessment of the physical properties inside the aneurysm pouch are crucial in understanding and predicting progression of the aneurysm and the associated risk of arterial wall rupture. Blood flow pattern assessment and local blood pressure measurements are supporting the physicians in taking a decision whether an aneurysm requires treatment. Typical treatments comprise placing coils into the aneurysm for breaking the flow pattern that is stretching the arterial wall, placement of blood flow diverters in the lumen of the arterial wall for impeding blood flow into the aneurysm, or a combination of the two in various phases of the treatment process.

Computational Fluid Dynamics (CFD) modeling by integrating patient-specific intravascular blood flow velocity and pressure measurements into computational models of aneurysms before and after treatment with flow-diverting stents is presented in "Cerebral Aneurysms Treated with Flow-Diverting Stents: Computational Models with Intravascular Blood Flow Measurements" by M. Levitt et al., American Journal of Neuroradiology, Vol. 35, issue 1, pages 143-148. The premise of aneurysmal flow diversion is the reduction of blood flow into the aneurysm dome, promoting intra-aneurysmal thrombosis and promoting endothelialization of the stent wall, which reconstructs the parent vessel, excluding the aneurysm. Reduction of hemodynamic stress is believed to be crucial in achieving this goal, and the determination of such stress is an important application of CFD analysis. In the method of hemodynamic stress computation three-dimensional rotational angiography is used, obtained before aneurysm treatment of patients. Contrast-enhanced flat panel Computer Tomography (CT) was obtained for stent visualization after treatment by endovascular flow-diverting stent placement. Blood flow velocity and blood pressure were measured before and after placement of flow-diverting stents by use of a dual-sensor pressure and Doppler velocity guidewire at essentially the same locations. The measurements were exported to a workstation for CFD analysis where the three-dimensional reconstructions of the vessels were created from the rotational angiographic images. A "virtual stent" was placed into each reconstruction for posttreatment simulations by inserting a saddle-shaped surface to the location of the stent boundary on the basis of its location in the posttreatment CT. In accordance with the therapeutic intent of flow-diverting stents, the results of the CFD model showed reduction of flow rate, vessel wall shear stress and shear stress gradient in the aneurysmal domes after treatment.

US 2005/0197571 A1 discloses an apparatus and method for the measurement of vascular impedance of the ocular circulation in vivo are provided. A pressure pulse waveform is recorded from measurement of the intraocular pressure, and the velocity profile of blood flow in the retrobulbar circulation is recorded. These two readings are used to calculate the vascular impedance modulus.

SUMMARY OF THE INVENTION

It is an object of the invention to provide an apparatus for improved characterization of a condition of a vessel wall of a living being.

According to a first aspect of the invention, this object is realized by an apparatus for characterizing a condition of a vessel wall of a living being, the apparatus comprising:
  a processor for processing measurement signals,
wherein the apparatus is configured to receive a temporal pressure measurement signal and a temporal flow measurement signal of a pulsatile blood motion within a vessel from at least an instrument trackable by an imaging unit with respect to a morphology of the vessel, and wherein the processor is configured to
    ascertain a phase difference between the temporal pressure measurement signal and the temporal flow measurement signal, indicative of the condition of the vessel wall.

A phase difference between a pulsatile blood pressure measurement signal and a pulsatile blood flow measurement signal within the vessel appears to be sufficient for a discrimination of a healthy vessel wall from a weakened one. This provides simplicity and an improved indication of vessel wall condition over flow pattern analysis based on CFD using angiographic information.

In a second aspect of the invention, a system for characterizing a condition of a vessel wall of a living being is presented, the system comprising:
  the apparatus according to the invention,
  the at least an instrument configured for providing the temporal pressure measurement signal of the pulsatile blood motion within the vessel, and
  the imaging unit configured for providing morphological information of the vessel,
  wherein the imaging unit or the at least an instrument is configured for providing the temporal flow measurement signal of the pulsatile blood motion within the vessel.

The pulsatile blood pressure measurement signal may be provided by a pressure sensor integrated into an interventional instrument, whereas the pulsatile blood flow measurement signal may either be a volumetric flow measurement with a suitable imaging unit or a blood flow velocity measurement provided by a suitable sensor integrated into the interventional instrument. The imaging unit may provide radiographic projections, computed tomography, ultrasound or magnetic resonance based morphological information. A weakened wall segment of the vessel can be identified and tagged on the display by tracking the position of the instrument with respect to the morphology of the vessel, and by knowing the phase difference between the pulsatile blood pressure and the pulsatile blood flow.

In an embodiment, the system further comprises a display, and the processor is configured for rendering a representation of the phase difference between the temporal pressure measurement signal and the temporal flow measurement signal on the display, indicative of the condition of the vessel wall. The visual representation of the phase difference may be a graphical representation of a superposition of the temporal pressure and flow measurement signals, a value indicating the phase difference in radians or a percentage of the phase difference relative to the period of the pulsatile blood motion.

In a further embodiment of the system, the processor is configured for rendering a morphological representation of the vessel on the display from the morphological information provided by the imaging unit. The structure of the vessel provides essential information for the physician during navigation of interventional instruments through vessels, in order to reach target sites in remote vasculature, for instance when the sites are located in peripheral and cerebral vasculature.

In a third aspect of the invention, an instrument for providing temporal pressure and flow measurement signals of a pulsatile blood motion within a vessel is presented, the instrument connectable to the apparatus according to the invention, the instrument comprising a pressure sensor and a flow sensor, wherein the pressure sensor and the flow sensor are located such as to provide temporal pressure and flow measurements in a same transversal plane of the instrument, wherein a position of the instrument is trackable by an imaging unit with respect to a morphology of the vessel. The benefit of using one and the same instrument for blood pressure and blood flow measurement, with sensors located in the same transversal plane of the instrument, is that in the process of ascertaining the phase difference between pulsatile pressure and flow, one can neglect the phase difference offset that would originate from the distance between the two measurement points along the blood vessel.

In a fourth aspect of the invention, a method of characterizing a condition of the vessel wall of the living being is presented, the method comprising:
receiving temporal pressure and flow measurement signals of a pulsatile blood motion within a vessel from at least an instrument trackable by an imaging unit with respect to a morphology of the vessel, and
ascertaining a phase difference between the temporal pressure measurement signal and the temporal flow measurement signal, indicative of a condition of the vessel wall.

In an embodiment, the method further comprises the step of rendering a representation of the phase difference between the temporal pressure measurement signal and the temporal flow measurement signal on a display, indicative of the condition of the vessel wall. Graphical or numerical visualization of the phase difference boosts visual interpretation of the results and improves assessment of the condition of the vessel wall segments.

In a further embodiment, the method comprises the steps of tracking a position of the at least an instrument with respect to the morphology of the vessel, and displaying the position of the at least an instrument on the morphological representation of the vessel. Position tracking of the measurement instrument with respect to the morphology improves the localization of the segments with weakened vessel wall, and provides supporting information for treatment decisions of those segments.

In yet a further embodiment, the method comprises positioning of the at least an instrument distal to an aneurysm with respect to a direction of the blood motion within the vessel based on tracking the position of the at least an instruments with respect to the morphology of the vessel. The method allows detection of an aneurysm in a vessel and evaluation of potential risks associated to vessel wall weakness.

In an embodiment, the method further comprises positioning of the at least an instrument distal to a flow diverting stent that is impeding at least partially blood flowing into the aneurysm based on tracking the position of the at least an instruments with respect to the morphology of the vessel. Flow diverting stents reduce hemodynamic stress of the already weak vessel wall of the aneurysm. The partial or complete occlusion of the aneurysm promotes intra-aneurysmal thrombosis and endothelialization of the stent wall. The outcome of flow diverting stent apposition can be efficiently evaluated from the phase difference between the pulsatile blood pressure and pulsatile blood flow measurement signals.

In a further embodiment, the method is used for vessel comprising coils inside the aneurysm. The long-term clinical outcome assessment of such a treatment and the risk evaluation for growth of the aneurysm based on CFD flow simulations relying on angiography are seriously hindered by the presence of coils in the aneurysm. Therefore, the method offers improved characterization of the condition of the vessel wall after coil placement into the aneurysm.

In an embodiment of the method, the temporal pressure and flow measurement signals are originating at the same distance from a neck of the aneurysm based on tracking the position of the at least an instruments with respect to the morphology of the vessel. The advantage is that there is no need for compensation for the temporal offset in the phase difference between pressure and flow measurement signals caused by the dissimilar distances between the locations of the pressure and flow measurements with respect to the weakened vessel wall.

Additional aspects and advantages of the invention will become more apparent from the following detailed description, which may be best understood with reference to and in conjunction with the accompanying drawings.

DETAILED DESCRIPTION OF EMBODIMENTS

Figure 1:
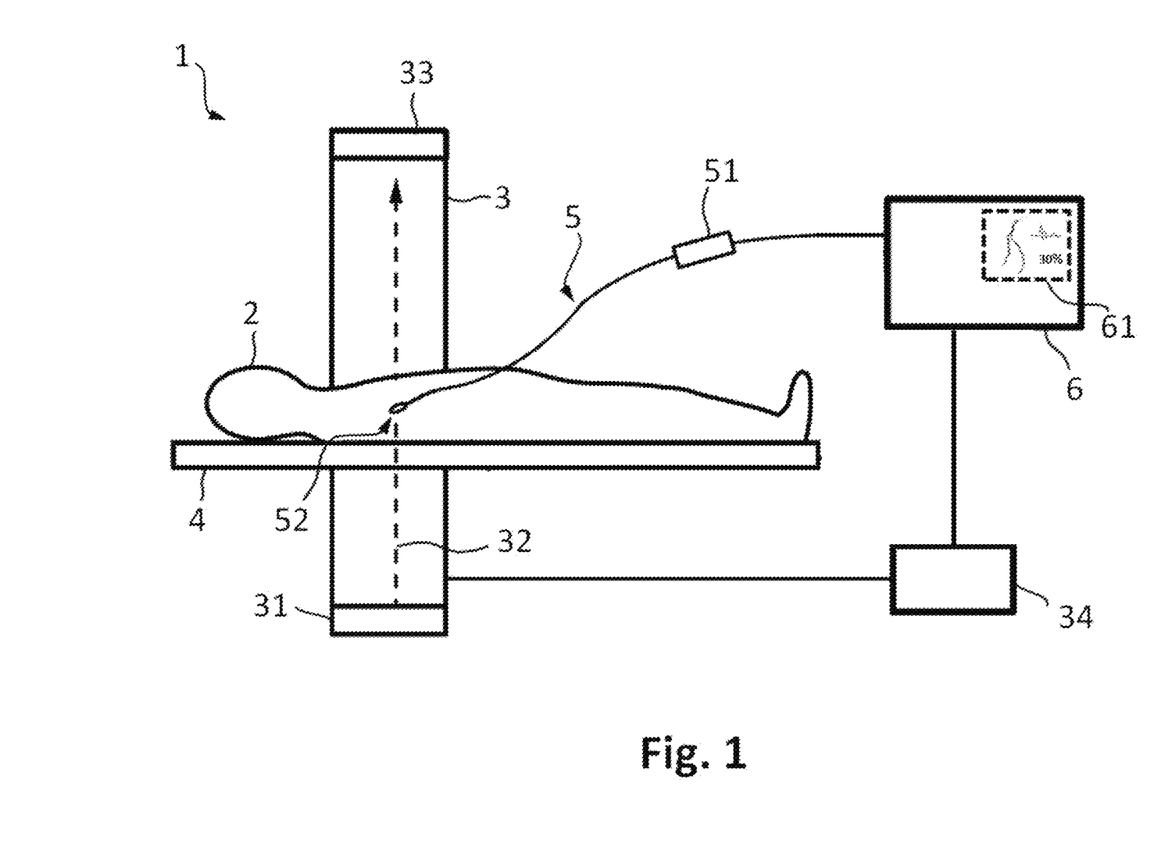
FIG. 1 shows schematically and exemplarily an embodiment of a system according to the invention.

FIG. 1 shows schematically and exemplarily an embodiment of a system 1 according to the invention, used for characterization of a condition of a vessel wall of a living being 2. In this embodiment, the system comprises a radiological imaging unit 3 for acquiring radiological angiographic (RA) projection of the vessel structure of interest upon injection of a contrast agent bolus in the targeted vasculature. The radiological imaging unit 3 comprises an x-ray source 31 for emitting x-rays 32 traversing the person 2 lying on the support means 4. The radiological imaging unit 3 further comprises an x-ray detector 33 for detecting the x-rays 32 after having traversed the person 2. The x-ray detector 33 is adapted to generate detection signals being indicative of the detected x-rays 32. The detection signals are transmitted to a fluoroscopy control unit 34, which is adapted to control the x-ray source 31, the x-ray detector 32 and to generate two-dimensional morphological projection information depending on the received detection signals. The injection of the radiological contrast agent bolus in the targeted vasculature is performed trough a lumen of the instrument 5, the lumen extending from the handgrip 51 to the distal tip 52 positioned at the target site in the vasculature. Alternatively, the instrument 5 may be introduced into the vasculature through the lumen of a tubular sheath, and the tubular sheath may be used for injection of the radiological contrast agent. Two-dimensional or three-dimensional morphology of the vasculature can be obtained with various techniques such as: magnetic resonance angiography (MRA) in which the imaging unit 3 is a magnetic resonance imaging system and the contrast agent is a gadolinium-based substance; ultrasound imaging (UI) in which the vasculature is imaged by using an extracorporal or intracorporal ultrasound imaging unit 3 while an echogenic contrast agent comprising microbubbles enhances the visibility of the vessels carrying blood; and computed tomography angiography (CTA) which is similar to RA. The instrument 5, which may be an interventional catheter, further comprises two sensors on its distal portion for providing measurement signals of physical properties of the blood within the vessel. An apparatus 6 receives the measurement signals and is adapted to render representations of the measurement signals or derived quantities on a display 61. The apparatus 6 may further be configured to render a representation of the morphology of the vessel on the display 61.

Figure 2:
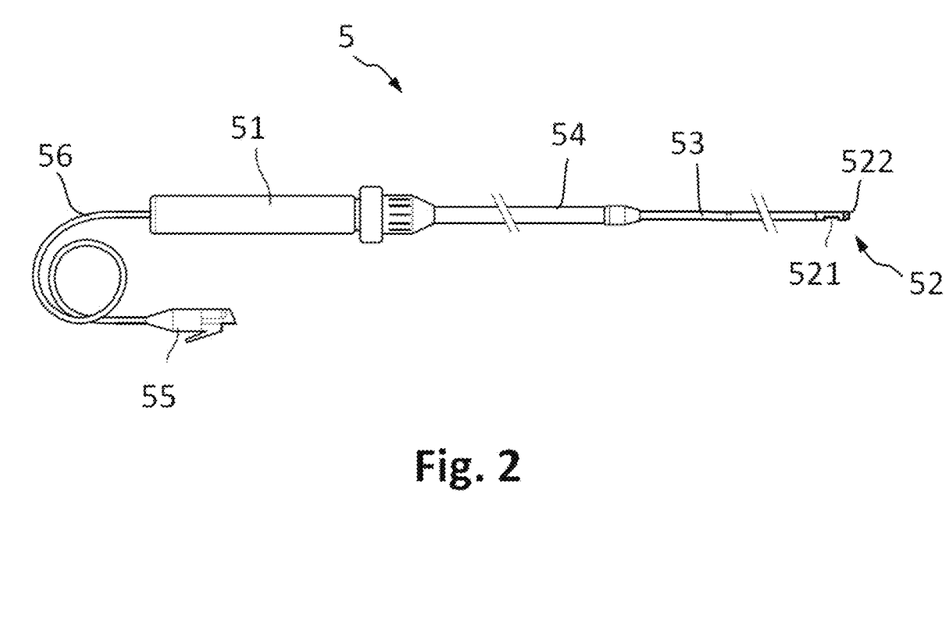
FIG. 2 shows schematically and exemplarily an embodiment of an instrument used for characterization of a vessel wall.

FIG. 2 shows an exemplarily embodiment of an instrument 5 used for assessment of the condition of the vessel wall. The instrument comprises a handgrip 51, a tubular elongated shaft 54, an extensible and more flexible shaft 53 reaching distal to the tubular elongated shaft 54, a connection cable 56 and a connector 55 for connecting the instrument to the apparatus 6. Alternatively, the instrument 5 may be only a guidewire comprising the flexible shaft 53, and the cable 56 may be a continuation of the guidewire, terminating at the proximal end with a connector 55 that is connectable to a patient interface module. In the guidewire configuration the instrument 5 is inserted into the vasculature of the patient through the lumen of an introducer sheath comprising the tubular handgrip 51 and the tubular elongated body 54. In the distal end 52 of the instrument 5 two sensors are integrated, a pressure sensor 521 and a flow sensor 522, similar to the configuration of the ComboWire® XT guidewire manufactured by Volcano Corporation. Typical pressure sensors use change of piezoresitive property upon pressure, fluidic transduction of a deflection of a diaphragm to a mechanical or an electrical signal, and capacitive readout of a suspended membrane over a substrate. Flow sensors integrated in interventional medical instruments typically use Doppler effect of ultrasound or laser radiation to measure blood flow velocity in vessels. The ultrasound waves for blood flow velocity measurement may be generated by piezoelectric ceramic (PZT) or plastic (PVDF) materials, as well as by capacitive or piezoelectric micromachined ultrasound transducers (cMUT or pMUT).

Figure 3:
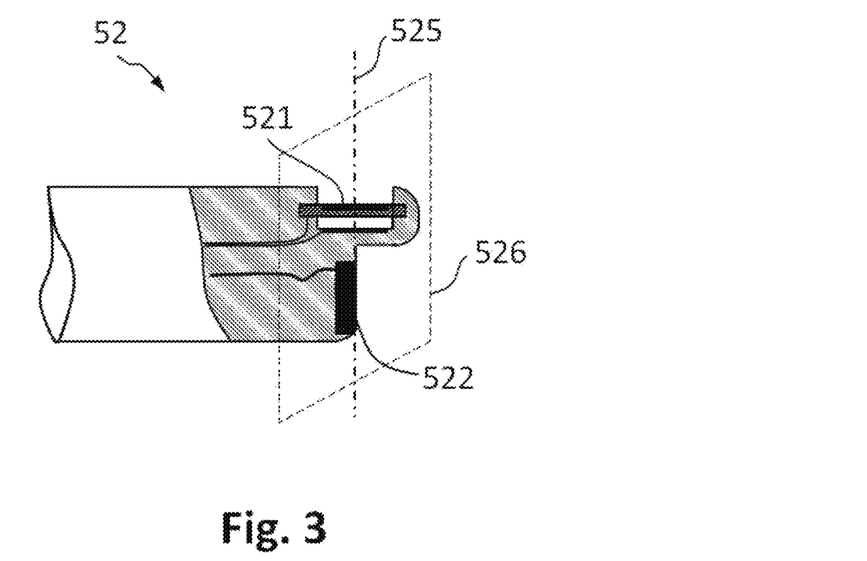
FIG. 3 shows an exemplary embodiment of the distal tip of the instrument.

In FIG. 3 an alternative embodiment of the distal tip 52 is schematically illustrated in a partial cross section of the instrument. A cMUT pressure sensor 521 comprising a membrane facing sideward is integrated into the distal tip 52, for allowing blood exerting pressure on the membrane. A piezoelectric ultrasound transducer 522 facing distal to the instrument is integrated for flow velocity measurement in the axial direction. A transversal plane 526 is defined by the longitudinal axis 525 of the cMUT pressure sensor. The sensors measure blood flow velocity and blood pressure in the same transversal plane 526 of the instrument 5, hence by placing the instrument into a vessel lumen then also in a single transversal plane of the vessel.

Figure 4:
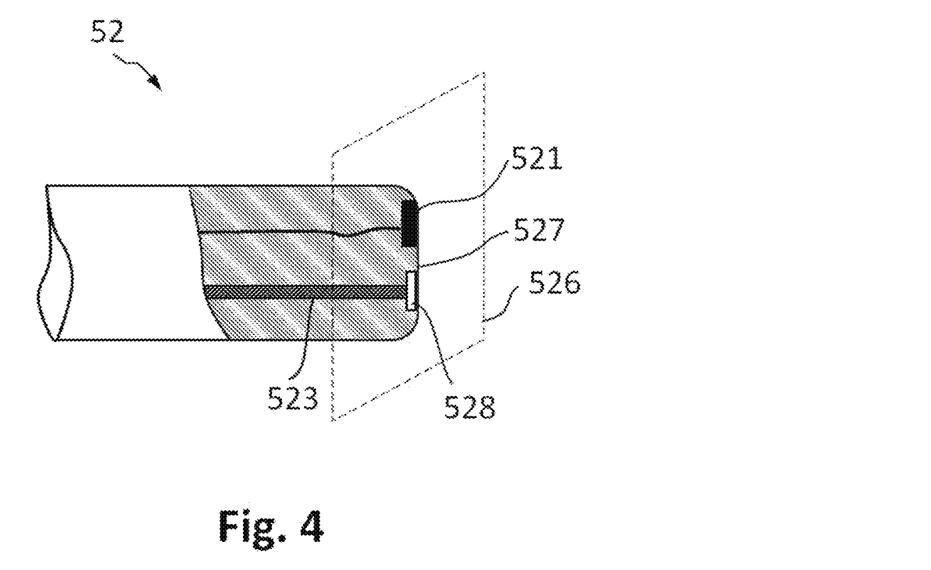
FIG. 4 shows an alternative embodiment of the distal tip.

An alternative embodiment of the distal tip 52 is schematically presented in FIG. 4. The piezoresistive pressure sensor 521 is integrated such that it measures blood pressure in a transversal plane 526 comprising the distal end 527 of the instrument 5. The pulsatile blood flow velocity is measured with an optical sensor comprising an optical fiber 523 integrated into the instrument. In this embodiment, the apparatus comprises a source for generating laser radiation that is transmitted through the optical fiber 523 to the distal portion 52 of the instrument. An optically transparent cavity 528 may separate the distal end of the optical fiber from the distal end 527 of the instrument. The cavity 528 may be of glass, transparent plastic or a compartment filled with optically transparent fluid. The apparatus 6 shown in FIG. 1 comprises a detector which detects the optical signals reflected back from the moving blood, and the processor derives the blood flow velocity from the frequency shift of the received laser radiation with respect to the transmitted one. Alternatively, the optical fiber 523 can be used for pressure measurement when the optically transparent cavity comprises a flexible membrane at the distal end 527 of the instrument. The pressure exerted on the distal end of the instrument causes a deflection of the membrane, and the optical path change of the laser reflection from the membrane is a measure of the exerted pressure for a known bending stiffness of the membrane. The optical path change may be measured by interferometry, wherein the reference optical path is defined by the reflection from the distal end of the optical fiber 823, and the changing optical path is defined by the reflection from one of the surfaces (internal or external) of the membrane closing the cavity at the distal end 527 of the instrument. As a further alternative, the single optical fiber 523 and the cavity 528 sealed by the membrane at the distal end 527 of the instrument 5 may be used simultaneously for blood pressure and blood flow velocity measurements, the deflection of the semitransparent membrane is the measure of the blood pressure exerted on the membrane, and the frequency shift of the laser radiation resulting from the motion of the blood distal to the instrument 5 is the measure of the blood flow velocity.

Although the pulsatile blood pressure has to be measured locally in the lumen of the vessel, the pulsatile blood flow can be derived from RA, CTA, MRA and UI. As an example, the pulsatile blood flow derived from RA is disclosed in Bonnefous et al, "Quantification of arterial flow using digital subtraction angiography", Medical Physics, Vol. 39, No. 10, p. 6264-75, 2012. The technique involves injection of iodine contrast medium at a very modest rate (e.g. 1.5 ml/s) into the vessel. As a consequence, the contrast agent is modulated by the flow pulsatility at the injection point driven by the cardiac cycle. The contrast is denser during the diastole phase and less dense during the systole phase. The modulated contrast agent pattern travels through the vessels. In the x-ray image, the contrast agent patterns can be followed along the vessel trajectory using an optical flow algorithm. By matching a 3D reconstruction of the vessel tree (e.g., obtained by 3D-RA) with the x-ray images, foreshortening can be taken into account, and the vessel diameters can be calculated. To determine the flow, the low frequent in- and out-flow of contrast medium is separated from the high frequent pulsatile components. The flow measurements need to be temporally synchronized to the pressure measurements from the instrument 5, which can be realized by synchronizing the injection of the contrast agent into the vessel with the pressure measurement. Optionally, it is possible to inject the contrast agent with the same system that measures the blood pressure (e.g. one unified guiding catheter/pressure guidewire assembly).

Figure 5:
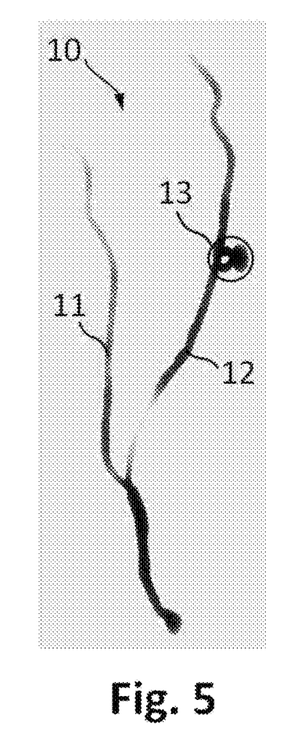
FIG. 5 shows an exemplary angiographic projection of a vasculature.
Figure 6:
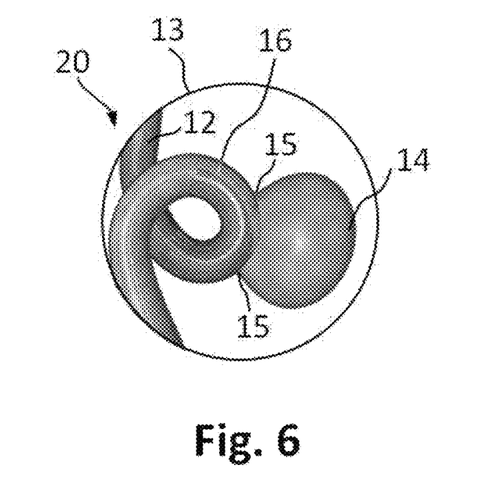
FIG. 6 shows an exemplary three-dimensional vessel morphology representation of a region from the angiographic projection.

FIG. 5 shows an angiographic projection 10 of a branching vessel, with a left branch 11 and a right branch 12. The right branch 12 comprises a loop and a bulge in the region 13 marked with a circle, for the exemplary description of the invention. A magnified three-dimensional vessel morphology representation 20 of the region 13 is reconstructed based on angiographic projections, which shows in FIG. 6 that the right vessel branch 12 comprises a region with weakened vessel wall that led to formation of an aneurysm 14. Typically, the aneurysm presents a circumferential neck 15, which represents the segment of weakened vessel wall. The three-dimensional model may further allow the possibility to customize a flow diverting stent 16 for treatment planning.

Figure 7:
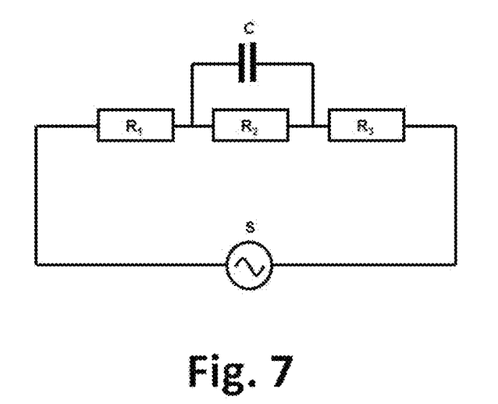
FIG. 7 shows schematically and exemplarily an embodiment of an equivalent electrical circuit of a vasculature network.

The vascular system can be represented in a simplified form as an equivalent electrical circuit of resistors and capacitors, whereby the vessels are represented by resistors and the aneurysms are represented by capacitors. The resistance of a single vessel is determined by its radius and its length. A vessel network can be collapsed into a single resistor. The capacity of the aneurysm is determined by its volume, its neck 15 area and its position. A vascular network with an aneurysm can be modelled as illustrated in FIG. 7. The oscillating source S represents the heart, which is the source of the periodic blood pressure with electrical equivalence of a potential, and the periodic blood flow with electrical equivalence of a current. Resistors $R_1$, $R_2$ and $R_3$ represent the resistance of the entire vascular network proximal to the aneurysm, the resistance of the vessel segment that holds the aneurysm 14, and the resistance of the entire vascular network distal to the aneurysm, respectively. Capacitor C models the influence of the aneurysm 14 on the blood flow. The complexity of the network may further be increased by addition of elements to the equivalent electrical circuit.

Figure 8A:
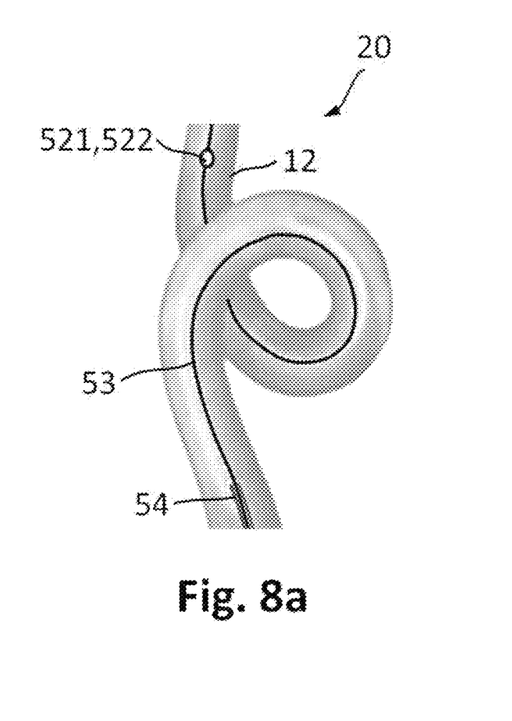
FIG. 8a shows an exemplary vessel morphology representation of a vessel with healthy vessel walls.

For a healthy vessel wall, schematically illustrated in FIG. 8a, the capacitor C is missing from the electrical network, due to the absence of an aneurysm. The blood pressure and blood flow are measured at the position of the sensors 521 and 522 in the vessel 12 with the instrument 5. Alternatively, the blood flow can be derived for the position of the blood pressure sensor from RA, CTA, MRA or UI, in which case the instrument 5 comprises only the pressure sensor 521, and the blood flow measurements are temporally synchronized to the pressure measurements. For a healthy vessel segment the current and the potential representing the blood flow and the blood pressure respectively, are in phase across the resistor $R_2$, as exemplarily illustrated in FIG. 8b. The pulsatile motion with a period T 620 is generated by cyclical heartbeat. The continuous line 621 represents the temporal blood pressure measurement signal and the dotted line 622 represents the temporal blood flow measurement signal.

Figure 9A:
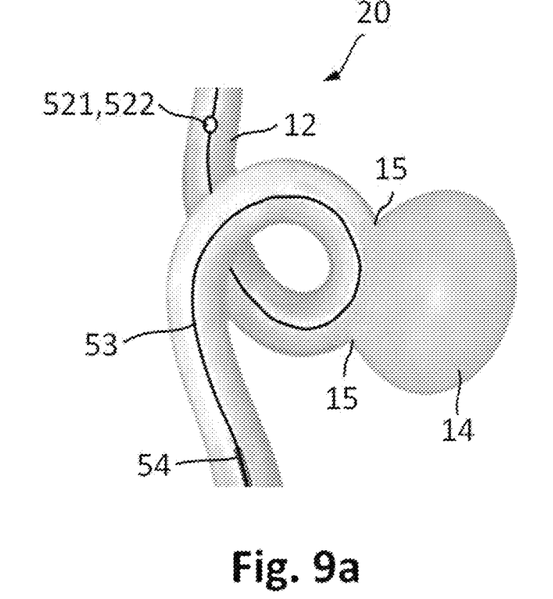
FIG. 9a shows an exemplary vessel morphology representation of a vessel comprising an aneurysm.

FIG. 9a shows an example of an aneurysm 14 formed due to a weakened segment of the vessel wall. The position of the distal tip 52 comprising the sensors 521,522 is distal to the aneurysm with respect to the direction of blood flow. Preferably, the measurement signals originate at the same distance from the neck 15 of the aneurysm 14, which can be provided with one of the embodiments of the instrument 5 shown in FIGS. 3, 4 or by a typical pressurewire (e.g. Verrata® Pressure Guide from Volcano Corporation) and one of the modalities from RA, CTA, MRA and UI used for deriving pulsatile blood flow.

Figure 9B:
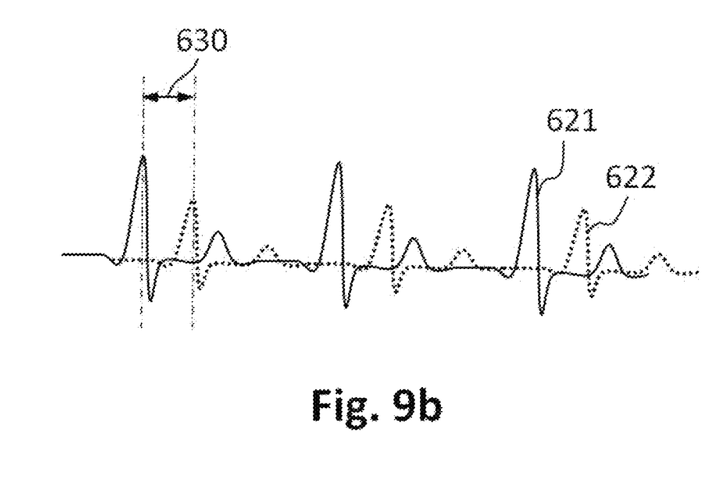
FIG. 9b shows an exemplary representation of the pulsatile blood pressure and pulsatile blood flow measurements for a vessel comprising an aneurysm.

The presence of the aneurysm causes a phase difference $\Delta t$ 630 between the measured blood pressure 621 and measured blood flow 622, as illustrated in FIG. 9b, similar to the phase difference between the potential and current measured between the resistors $R_2$ and $R_3$ in the equivalent electrical circuit. The measure of the phase difference is indicative of the condition of the vessel wall, hence the size of the aneurysm. For detection of the phase difference 630 it is not essential to accurately measure the absolute values of pulsatile blood pressure and pulsatile blood flow, since the pulsatility is easily derivable from relative blood pressure and blood flow measurement signals. Therefore, calibration of the measurements is not necessary, which is a major advantage of the technique.

Figure 10A:
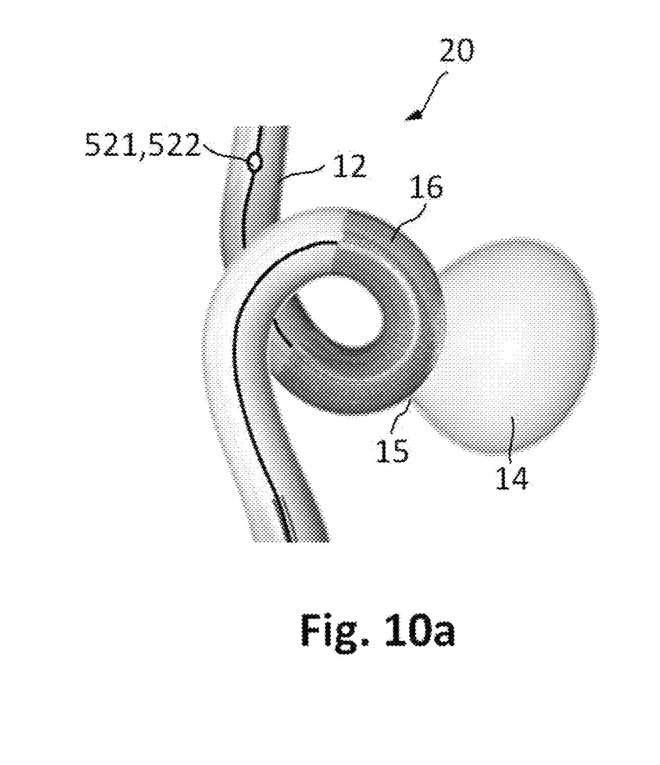
FIG. 10a shows an exemplary vessel morphology representation of a vessel treated by flow diverting stent apposition.
Figure 10B:
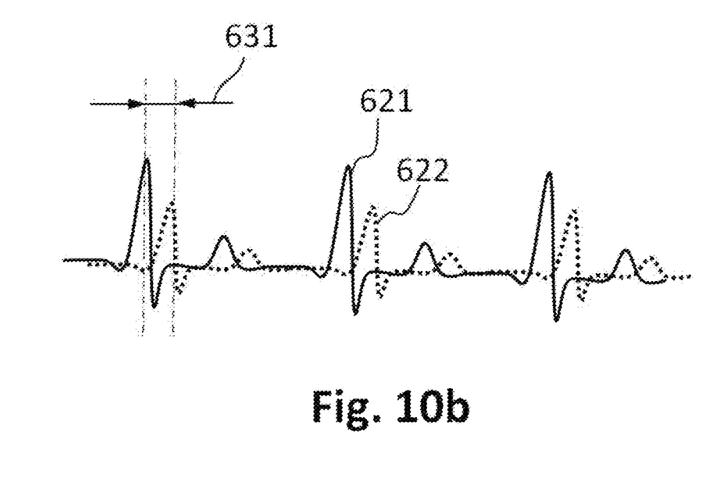
FIG. 10b shows an exemplary representation of the pulsatile blood pressure and pulsatile blood flow measurements for a vessel treated by flow diverting stent apposition.

Typical treatment of an aneurysm is flow diverting stent apposition into the vessel, such that the weakened vessel segment and adjacent portions proximal and distal to the weakened segment are covered and protected from further weakening. FIG. 10a shows an example of a stent 16 limiting blood flowing into the aneurysm 14. The stent prevents in the first instance the evolution of the aneurysm to a larger size, leading to increased risk of aneurysm rupture, and secondly, it permits the blood already present within the aneurysm to clot and form further protection of the already weak vessel wall. Placing a flow diverting stent 16 reduces the capacitance C of the aneurysm in the equivalent electrical circuit, with the consequence that the phase difference between the potential and the current reduces. FIG. 10b shows the effect of a flow diverting stent apposition on the measured blood pressure 621 and blood flow 622. The change of the phase difference prior and post flow diverting stent apposition (630 compared to 631) is a measure of stent placement efficacy, as an incorrectly placed stent has less impact on the capacitance C of the aneurysm 14. The expected outcome of the treatment is that the aneurysm stops evolving, and the clotted blood completely blocks and protects the wall of the aneurysm. Therefore, in a follow-up examination of the patient, the phase difference 631 is expected to further decrease, potentially showing no phase difference after a longer duration.

Figure 11:
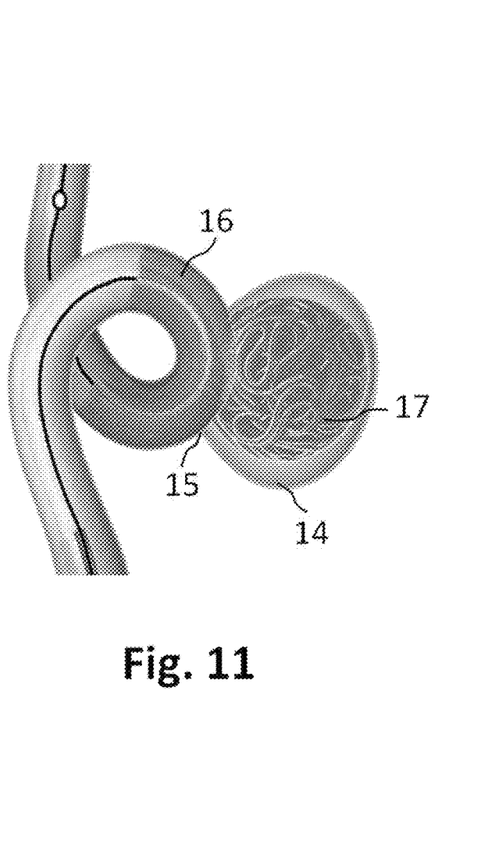
FIG. 11 shows an exemplary vessel morphology representation of a vessel treated by placement of coils into the aneurysm prior to apposition of a flow diverting stent.

An alternative, but less efficient treatment of the aneurysm is placement of multiple coils within the aneurysm, with the intent to limit blood flowing into the aneurysm by decreasing the available volume of the aneurysm pocket. In case that the treatment is not successful and the aneurysm keeps evolving in size, flow diverting stent apposition is necessary. The coil placement is just very locally addressing the problem, whereas the flow diverting stent protects vessel wall segments proximal and distal to the aneurysm, which might also exhibit poor condition. An example of an aneurysm 14 treated by placement of coils 17 prior to flow diverting stent 16 apposition is shown in FIG. 11, wherein the aneurysm in the vessel model has been partially sectioned for making coils 17 visible in the illustration.

Figure 8B:
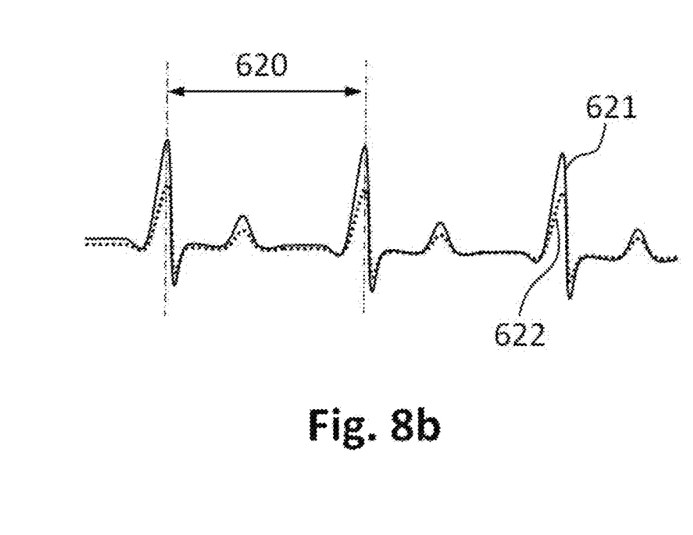
FIG. 8b shows an exemplary representation of a pulsatile blood pressure and a pulsatile blood flow measurement for a vessel with healthy vessel walls.

Once the processor ascertains the phase difference 630, 631 between the measured pulsatile blood pressure 621 and pulsatile blood flow 622 signals, the processor may render a graphical representation as presented in FIGS. 8b, 9b, 10b on the display 61 integrated into the apparatus 6, or on a separate screen available for the physician. Alternatively or additionally, the display may present values corresponding to the phase difference Δt, or a percentage of the phase difference with respect to the period T between consecutive heartbeats. The processor may render on the display 61 a morphological representation 20 of the vessel structure from information received from the imaging unit 3. The imaging unit 3 may further provide information on the position of the instrument 5 with respect to the morphology of the vasculature. Tracking of the distal tip 52 of the instrument 5 in RA or in CTA can be achieved by using radiological marker integrated into the distal tip. Alternatively, in UI the tracking of the position of the instrument 5 can be realized by integrating active ultrasound sensor into the distal tip. The ultrasound sensor transmits ultrasound waves from within the vessel through the body of the patient 2 and a portion of the ultrasound signal is received by the intracorporal or extracorporal ultrasound imaging unit 3, which is also providing the morphological information of the target vasculature in its field of view, enabling continuous localization of the distal tip 52 within the vessel morphology. Visualization of the position of the sensors 521, 522 and/or instrument 5 on the morphological representation 20 may be illustrated as in FIGS. 8a, 9a, 10a. A weakened segment of the vessel wall can be identified and tagged on the display by tracking the position of the instrument with respect to the morphology of the vessel, and by knowing the phase difference between the pulsatile blood pressure and the pulsatile blood flow.

Figure 12:
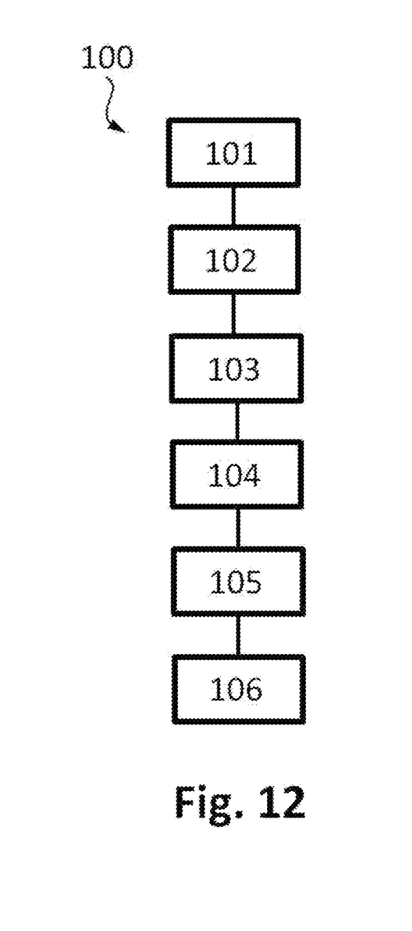
FIG. 12 shows schematically a method for characterizing the condition of the vessel wall of a patient.

FIG. 12 illustrates schematically a method 100 of characterizing the condition of the vessel wall of a patient. In step 101 the apparatus 6 receives temporal pressure 621 and flow 622 measurement signals of a pulsatile blood motion within the vessel, and in step 102 the processor of the apparatus 6 ascertains the phase difference 630,631 between the pulsatile blood pressure measurement signal 621 and the pulsatile blood flow measurement signal 622, indicative of the condition of the vessel wall. Preferably, the sensors providing the measurement information are integrated into the instrument 5 as shown in FIGS. 3 and 4, such as to provide blood pressure 621 and blood flow 622 measurements in the same transversal plane 526 of the instrument. The pressure and blood flow measurements may alternatively be performed with an instrument as shown in FIG. 2, where the two sensors are not providing measurements in the same transversal plane of the vessel. As a consequence, the measurement of either the blood pressure or that of the blood flow has to be compensated for the phase offset originating from the known distance between the two sensors 521,522 integrated into the distal tip 52. Alternatively, two different instruments may be inserted into the vessel, each one comprising a single sensor, hence the pressure measurement can be carried out with a pressurewire (e.g. Verrata® from Volcano Corporation), and the blood flow can be measured with a Doppler guidewire (e.g. FloWire® from Volcano Corporation). In an embodiment of the method, the pressure is measured with a pressurewire and the blood flow is measured with an imaging unit 3 related to one of the blood flow imaging modalities RA, CTA, MRA, UI. The method further comprises the step 103 of rendering a representation of the phase difference 630 between the pulsatile blood pressure measurement signal 621 and the pulsatile blood flow measurement signal 622 on a display 61, indicative of the condition of the vessel wall. In step 104 the processor of the apparatus 6 is configured to render a morphological representation 20 of the vessel on the display 61 from the morphological information provided by the imaging unit 3. In step 105 the imaging unit 3 is tracking the position of the instrument 5 with respect to the morphology of the vessel, and in step 106 the position of the instrument 5 is displayed on the morphological representation 20 of the vessel.

In an embodiment of the method 100, the temporal pressure 621 and flow 622 measurement signals originate from a vessel comprising an aneurysm 14 in the vessel wall, and the measurement signals originate distal to the aneurysm 14 with respect to a direction of the blood flow. Measurements proximal to the aneurysm would potentially show no phase difference between the pulsatile pressure and blood flow, indicative of healthy vessel wall, unless yet another aneurysm is present proximal to the respective measurement location. The method allows detection of vessel wall weakness along the vessel during pullback of the instrument 5 comprising both pressure and flow sensors, or by pulling back the instrument comprising only the pressure sensor and by measuring the blood flow with the imaging unit 3 along the tracked trajectory of the pulled back instrument. The pullback rate should be such to allow sufficient time to determine the potential presence of phase difference 630 in the discrete measurement locations along the pullback trajectory of the instrument.

In an embodiment, the method 100 is used for assessing the efficacy of flow diverting stent 16 apposition. The flow diverting stent obstructs at least partially blood flowing into the aneurysm in order to reduce the cyclical pressure stretching the aneurysm wall. Reduction of blood flow into the aneurysm also promotes intra-aneurysmal thrombosis. An accurate apposition of the flow diverting stent is detectable by a significant reduction of post apposition phase difference 631 between the pulsatile pressure 621 and pulsatile blood flow 622 measurement signals with respect to the phase difference 630 prior to stent apposition.

The method 100 may be used for assessing efficacy of flow diverting stent 16 apposition after an initial treatment of coil 17 placement into the aneurysm 14. A potential weakness of the treatment with coils is that on a longer term the vessel wall in the vicinity of the initial neck 15 of the aneurysm may further weaken. A correctly appositioned stent protects the neck 15 of the aneurysm 14 and also the vessel wall in the vicinity proximal and distal to the aneurysm neck 15.

In an embodiment of the method 100, the temporal pressure 621 and flow 622 measurement signals preferably originate at the same distance from the neck 15 of the aneurysm 14, with the advantage that there is no temporal offset caused by the dissimilar distances between the locations of the pressure and blood flow measurements with respect to the aneurysm neck 15.

Although medical device was used in the exemplary description of the invention, that should not be construed as limiting the scope.

Other variations to the disclosed embodiments can be understood and effected by those skilled in the art in practicing the claimed invention, from a study of the drawings, the disclosure, and the appended claims.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. An instrument configured for insertion into a vessel, the instrument comprising:
a pressure sensor integrated into the instrument, the pressure sensor configured to provide temporal pressure measurement signals of pulsatile blood motion within the vessel; and
a flow sensor integrated into the instrument, the flow sensor configured to provide temporal flow measurement signals of the pulsatile blood motion within the vessel,
wherein the pressure sensor and the flow sensor are arranged on the instrument to provide the temporal pressure measurement signals and the temporal flow measurement signals in a same transversal plane of the instrument, and
wherein the instrument is connectable to a processor configured to detect a condition of a segment of the vessel by determination of a phase difference between the temporal pressure measurement signals and the temporal flow measurement signals.

2. The system according to claim 1, wherein:
the instrument is configured to acquire the temporal pressure measurement signals and the temporal flow measurement signals along a trajectory of the instrument during a pullback motion within the vessel; and
the processor is configured to ascertain the phase difference between the temporal pressure measurement signals and the temporal flow measurement signals at discrete measurement locations along the trajectory of the instrument.

3. The system according to claim 1, further comprising a display, and wherein the processor is configured to render a representation of the phase difference between the temporal pressure measurement signals and the temporal flow measurement signals on the display, indicative of the condition of the vessel wall.

4. The system according to claim 1, further comprising an imaging system configured to provide morphological information of the vessel and to track a position of the instrument with respect to the morphology morphological information of the vessel.

5. The system according to claim 4, further comprising a display, and wherein the processor is configured to output to the display the detected condition of the segment of the vessel with respect to a morphological representation of the vessel.

6. The system according to claim 5, wherein the processor is configured to output to the display the position of the instrument on the morphological representation of the vessel.

7. A method of characterizing a condition of a vessel wall, the method comprising:
inserting an instrument into a vessel;
receiving temporal pressure measurement signals of a pulsatile blood motion within the vessel from the instrument;
receiving temporal flow measurement signals of the pulsatile blood motion within the vessel from the instrument, wherein the temporal pressure measurement signals and the temporal flow measurement signals are measured in a same transversal plane of the instrument;
ascertaining a phase difference between the temporal pressure measurement signals and the temporal flow measurement signals; and
detecting, by the phase difference, a condition of a segment of the vessel wall.

8. The method according to claim 7, further comprising:
receiving the temporal pressure measurement signals and the temporal flow measurement signals of the pulsatile blood motion within the vessel from the instrument along a trajectory of the instrument during a pullback motion within the vessel; and
ascertaining the phase difference between the temporal pressure measurement signals and the temporal flow measurement signals, indicative of the condition of the segment of the vessel wall, at discrete measurement locations along the trajectory of the instrument.

9. The method according to claim 7, further comprising:
rendering a representation of the phase difference between the temporal pressure measurement signals and the temporal flow measurement signals on a display, indicative of the condition of the segment of the vessel wall.

10. The method according to claim 7, further comprising:
providing morphological information of the vessel; and
tracking a position of the instrument with respect to a morphology of the vessel based on the morphological information of the vessel.

11. The method according to claim 10, further comprising:
rendering, on a display, a representation of the detected condition of the segment of the vessel wall with respect to a morphological representation of the vessel.

12. The method according to claim 10, further comprising:

displaying, on a display, the position of the instrument with respect to a morphological representation of the vessel.

13. The method according to claim 10, further comprising:
positioning the instrument distal to an aneurysm with respect to a direction of the pulsatile blood motion within the vessel based on tracking the position of the instrument with respect to the morphology of the vessel.

14. The method according to claim 13, further comprising:
positioning the instrument distal to a flow diverting stent impeding at least partially blood flowing into the aneurysm based on tracking the position of the instrument with respect to the morphology of the vessel.

15. The method according to claim 14, wherein the method is used for the vessel comprising coils inside the aneurysm.

16. A non-transitory computer-readable storage medium having stored a computer program comprising instructions, which, when executed by a processor, cause the processor to:
receive temporal pressure measurement signals of a pulsatile blood motion within a vessel from an instrument inserted into the vessel;
receive temporal flow measurement signals of the pulsatile blood motion within the vessel from the instrument, wherein the temporal pressure measurement signals and the temporal flow measurement signals are measured in a same transversal plane of the instrument;
ascertain a phase difference between the temporal pressure measurement signals and the temporal flow measurement signals; and
detect, by the phase difference, a condition of a segment of the vessel wall.

17. The non-transitory computer-readable storage medium according to claim 16, wherein the instructions, when executed by the processor, further cause the processor to:
render, on a display, a representation of the phase difference between the temporal pressure measurement signals and the temporal flow measurement signals.

18. The non-transitory computer-readable storage medium according to claim 16, wherein the instructions, when executed by the processor, further cause the processor to:
provide morphological information of the vessel; and
track a position of the instrument with respect to the morphology morphological information of the vessel.

19. The non-transitory computer-readable storage medium according to claim 18, wherein the instructions, when executed by the processor, further cause the processor to at least one of:
render, on a display, a representation of the detected condition of the segment of the vessel wall with respect to a morphological representation of the vessel, and
render, on the display, the position of the instrument with respect to the morphological representation of the vessel.

* * * * *